United States Patent
Monda et al.

(10) Patent No.: US 11,090,246 B2
(45) Date of Patent: Aug. 17, 2021

(54) POWDER HAIR DYE COMPOSITION

(71) Applicant: KAO CORPORATION, Tokyo (JP)

(72) Inventors: Keiji Monda, Katsusika-ku (JP); Takeshi Iizaki, Saitama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/648,904

(22) PCT Filed: Sep. 20, 2018

(86) PCT No.: PCT/JP2018/034756
§ 371 (c)(1),
(2) Date: Mar. 19, 2020

(87) PCT Pub. No.: WO2019/059261
PCT Pub. Date: Mar. 28, 2019

(65) Prior Publication Data
US 2020/0246239 A1 Aug. 6, 2020

(30) Foreign Application Priority Data
Sep. 20, 2017 (JP) .............................. JP2017-180754

(51) Int. Cl.
| | | |
|---|---|---|
| *A61Q 5/10* | (2006.01) | |
| *A61K 8/49* | (2006.01) | |
| *A61K 8/02* | (2006.01) | |
| *A61K 8/25* | (2006.01) | |
| *A61K 8/73* | (2006.01) | |
| *A61K 8/92* | (2006.01) | |
| *A61K 8/96* | (2006.01) | |

(52) U.S. Cl.
CPC ................ *A61K 8/49* (2013.01); *A61K 8/022* (2013.01); *A61K 8/25* (2013.01); *A61K 8/732* (2013.01);
(Continued)

(58) Field of Classification Search
CPC . A61Q 5/10; A61Q 5/065; A61K 8/49; A61K 8/92; A61K 8/732; A61K 8/022;
(Continued)

(56) References Cited
U.S. PATENT DOCUMENTS

2004/0019982 A1* 2/2004 Pratt ...................... A61K 8/492
8/405
2004/0055094 A1 3/2004 Massoni
(Continued)

FOREIGN PATENT DOCUMENTS

DE  10 2005 013 488 A1  9/2006
EP      2 883 530 A1    6/2015
(Continued)

OTHER PUBLICATIONS

International Search Report dated Dec. 21, 2018 in PCT/JP2018/034756 filed on Sep. 20, 2018.

*Primary Examiner* — Eisa B Elhilo
(74) *Attorney, Agent, or Firm* — Oblon, McClelland, Maier & Neustadt, L.L.P.

(57) ABSTRACT

A powder hair dye composition, containing the following components (A) to (C): (A) one or more azo dyes selected from the group consisting of the following (A-1), (A-2) and (A-3), (B) an alkaline agent other than alkanolamines, and (C) 1.5 mass % or more and 40 mass % or less of solvent.

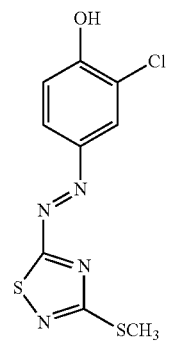

(A-1)

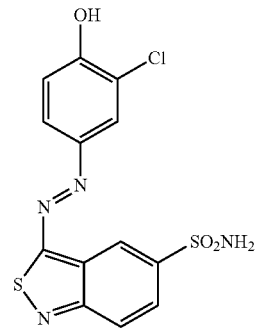

(A-2)

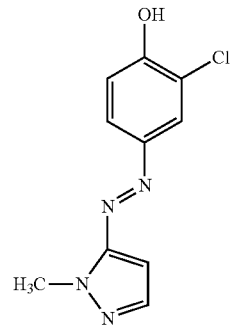

(A-3)

12 Claims, No Drawings

(52) U.S. Cl.
CPC ................ *A61K 8/92* (2013.01); *A61K 8/965* (2013.01); *A61K 2800/432* (2013.01); *A61K 2800/48* (2013.01)

(58) Field of Classification Search
CPC . A61K 8/25; A61K 2800/432; A61K 2800/48
USPC ..................................................... 8/405, 437
See application file for complete search history.

(56) References Cited

U.S. PATENT DOCUMENTS

| | | |
|---|---|---|
| 2016/0235634 A1 | 8/2016 | Sato et al. |
| 2017/0196791 A1* | 7/2017 | Nojiri ..................... A61K 8/43 |
| 2017/0196792 A1 | 7/2017 | Nojiri |

FOREIGN PATENT DOCUMENTS

| | | |
|---|---|---|
| EP | 3 056 190 A1 | 8/2016 |
| EP | 3 153 153 A1 | 4/2017 |
| JP | 2002-97120 A | 4/2002 |
| JP | 2003-342139 A | 12/2003 |
| JP | 2019-55944 A | 4/2019 |
| JP | 2019-55945 A | 4/2019 |
| JP | 2019-55946 A | 4/2019 |
| JP | 2019-151615 A | 9/2019 |
| JP | 2019-151616 A | 9/2019 |

\* cited by examiner

POWDER HAIR DYE COMPOSITION

TECHNICAL FIELD

The present invention relates to a powder hair dye composition.

BACKGROUND ART

Hair dye compositions containing a direct dye such as an acidic dye, a basic dye or a nitro dye are widely known. When the hair dye composition containing a direct dye is a liquid and the direct dye contained is not sufficiently soluble in water or other solvents, the direct dye, if contained in a high concentration, may precipitate in the hair dye composition during storage. In such a hair dye composition, lower concentration of a direct dye in the composition may decrease the amount of the direct dye to penetrate in the hair, thus impairing dyeability and/or providing a dyed hair color that is different from as intended.

Techniques free from the above problem caused by low solubility include a hair dye composition containing a direct dye in the form of powder, which can be used, for example, in a method by which the hair dye composition is mixed with water or other solvents before use (see PTL 1), and in a method by which the hair dye composition is mixed with another bleaching agent or another hair dye agent to be used (see PTL 2).

(PTL 1) JP 2002-97120 A
(PTL 2) EP 2883530 B

SUMMARY OF INVENTION

The present invention provides a powder hair dye composition comprising the following components (A) to (C):

(A) one or more azo dyes selected from the group consisting of the following (A-1), (A-2) and (A-3):

[Chem. 1]

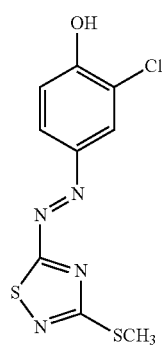

(A-1)

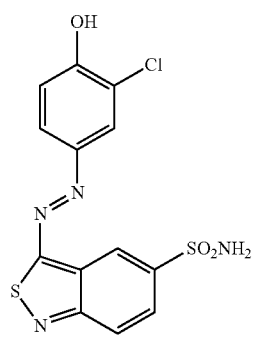

(A-2)

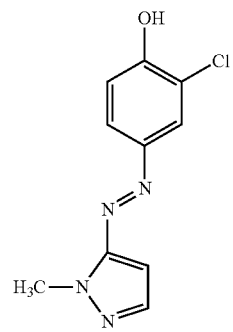

(A-3)

(B) an alkaline agent other than alkanolamines, and
(C) 1.5 mass % or more and 40 mass % or less of solvent.

DETAILED DESCRIPTION OF THE INVENTION

Some direct dyes in a form of powder may give a greatly different hair color after hair dyeing from the color of the powder composition. This can make it difficult to tone color based on intended hair color after hair dyeing.

The present invention relates to a powder hair dye composition containing a direct dye, which is dissolved before use, with which the hair dyeing properties are freely controllable, thus facilitating toning operation based on imagined hair color after hair dyeing.

The present inventors found that a specific azo dye, mixed with an alkaline agent, can provide a powder hair dye composition having a color close to a color exhibited on hair after hair dyeing.

The present invention provides small difference between a color of a powder hair dye composition and a color of hair after hair dyeing, thus facilitating a toning operation on the basis of imagination of the hair color after hair dyeing.

(Component (A): Azo Dye)

The powder hair dye composition of the present invention contains one or more azo dyes selected from the group consisting of the following (A-1), (A-2) and (A-3) as the component (A).

[Chem. 2]

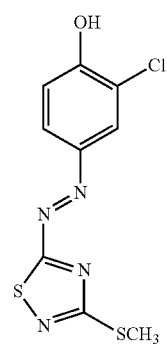

(A-1)

-continued

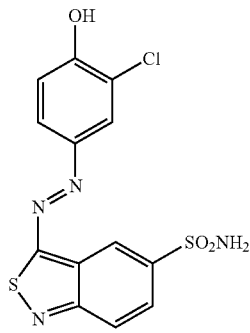

(A-2)

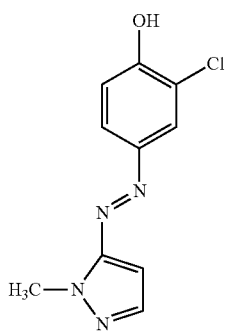

(A-3)

The pKa of the azo dyes (A-1), (A-2) and (A-3) is 6.0, 6.0 and 7.5 respectively, and by dissociation of a proton, (A-1) assumes red color, (A-2) assumes blue color, and (A-3) assumes yellow color. Therefore, because the components (B) and (C) coexist with the component (A) in the powder hair dye composition of the present invention, a proton of the component (A) is dissociated and a color of the composition becomes close to one after hair dyeing.

The total content of component (A) in the powder hair dye composition of the present invention is preferably 0.1 mass % or more, more preferably 0.5 mass % or more, further preferably 1.0 mass % or more, further preferably 3.0 mass % or more and further preferably 5.0 mass % or more from the viewpoint of imparting sufficient hair dyeing properties, and also preferably 50 mass % or less, more preferably 30 mass % or less, and further preferably 20 mass % or less from the viewpoint of ease of measurement and mixing.

(Component (B): Alkaline Agent)

The powder hair dye composition of the present invention contains, as component (B), an alkaline agent other than alkanolamines in order to dissociate a proton from component (A) and approximate a color of the composition to a color of hair after hair dyeing. Examples of the alkaline agent include metasilicates such as sodium metasilicate and potassium metasilicate; alkali metal hydroxides such as sodium hydroxide and potassium hydroxide; alkaline earth metal hydroxides such as calcium hydroxide; alkanediamines such as 1,3-propanediamine and salts thereof; carbonates such as sodium carbonate, potassium carbonate and guanidine carbonate; and hydrogencarbonates such as sodium hydrogencarbonate and potassium hydrogencarbonate, and one or more selected from these are used. Among these, one or more selected from alkali metal hydroxides are preferable from the viewpoint of approximating a color of the composition to a color of hair after hair dyeing, and sodium hydroxide and potassium hydroxide are more preferable. These components (B) can be used individually or two or more components (B) can be used in combination.

The content of component (B) in the powder hair dye composition of the present invention is preferably 0.1 mass % or more, more preferably 0.2 mass % or more, further preferably 0.3 mass % or more, further preferably 0.5 mass % or more, further preferably 1.0 mass % or more, and further preferably 1.5 mass % or more from the viewpoint of approximating a color of the composition to a color of hair after hair dyeing, and also preferably 40 mass % or less, more preferably 30 mass % or less, further preferably 25 mass % or less, and further preferably 20 mass % or less from the viewpoint of reducing hair damage and scalp stimulation.

(Component (C): Solvent)

The powder hair dye composition of the present invention contains, as component (C), 1.5 mass % or more and 40 mass % or less of solvent to dissociate a proton from the component (A) and approximate a color of the composition to a color of hair after hair dyeing. For the solvent, water or organic solvents can be used, and for the organic solvents, water-soluble ones are preferable. Examples of such water-soluble organic solvents include methanol, ethanol, n-propanol, isopropanol, n-butanol, isobutanol, ethylene glycol, propylene glycol, dipropylene glycol, 1,3-butylene glycol, ethylene glycol monoethyl ether, acetone, diethyl ether, tetrahydrofuran, and diacetone alcohol. These components (C) can be used individually or two or more components (C) can be used in combination. As the component (C), water and a mixed liquid of water and a water-soluble organic solvent are preferable.

The content of component (C) in the powder hair dye composition of the present invention is 1.5 mass % or more, preferably 2 mass % or more, more preferably 3 mass % or more, and further preferably 5 mass % or more from the viewpoint of approximating a color of the composition to a color of hair after hair dyeing, and also 40 mass % or less, preferably 35 mass % or less, more preferably 30 mass % or less, and further preferably 25 mass % or less from the viewpoint of maintaining the powder form of the composition.

(Component (D): Powder Carrier)

The powder hair dye composition of the present invention preferably contains a powder carrier as component (D), and the component (A), (B) and (C) are preferably carried by component (D). As the powder carrier, any of organic and inorganic powders can be used as long as it does not react with the component (A), (B) and (C). Specific examples of the powder carrier include silica (silicon dioxide), diatomaceous earth, kaolin, bentonite, cornstarch, tapioca starch, rice starch, wheat starch, potato starch, nylon powder, montmorillonite, gypsum, sawdust, and pearlite. Among these, corn starch, diatomaceous earth and silica are preferable. These components (D) can be used individually or two or more components (D) can be used in combination.

The content of component (D) in the powder hair dye composition of the present invention is preferably 10 mass % or more, more preferably 30 mass % or more, and further preferably 40 mass % or more from the viewpoint of preparing the composition in a powder form, and also preferably 90 mass % or less, more preferably 80 mass % or less, and further preferably 70 mass % or less from an economic point of view.

The hair dye composition of the present invention can also contain a direct dye other than azo dyes (A-1), (A-2) and (A-3). The total content of azo dye (A-1), (A-2) and (A-3) is preferably 1 mass % or more and 100 mass % or less, more preferably 5 mass % or more and 100 mass % or less, further more preferably 10 mass % or more and 100 mass % or less, and further more preferably 20 mass % or more and 100 mass % or less of all dyes from the viewpoint of maintaining the dyeability of the component (A).

Examples of direct dyes other than the component (A) include anionic dyes, cationic dyes and neutral dyes. Examples of anionic dyes include, Acid Black 1, Acid Blue 1, Acid Blue 3, Food Blue No. 2, Food Blue No. 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, Acid Orange 24, Acid Green 25, Solvent Green 7, Solvent Red 73, Acid Red 95, Solvent Red 43, Solvent Red 48, Acid Red 33, Solvent Violet 13, Acid Yellow 73, Food Red No. 17, Food Red No. 1, Food Yellow No. 3, Food Blue No. 2, Food Black No. 1, Food Black No. 2, Disperse Black 9, Disperse Violet 1, and their alkali metal salts (sodium salt and potassium salt). Examples of cationic dyes include, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12, Basic Red 22, Basic Red 76, Basic Violet 1, Basic Violet 2, Basic Violet 3, Basic Violet 10, Basic Violet 14, Basic Yellow 57, Basic Red 51, Basic Yellow 87, Basic Blue 17, and Basic Orange 31. Examples of neutral dyes include, HC Blue 2, HC Blue 4, HC Blue 5, HC Blue 6, HC Blue 7, HC Blue 8, HC Blue 9, HC Blue 10, HC Blue 11, HC Blue 12, HC Blue 13, HC Brown 1, HC Brown 2, HC Green 1, HC Orange 1, HC Orange 2, HC Orange 3, HC Orange 5, HC Red BN, HC Red 1, HC Red 3, HC Red 7, HC Red 8, HC Red 9, HC Red 10, HC Red 11, HC Red 13, HC Red 54, HC Red 14, HC Violet BS, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, 2-amino-6-chloro-4-nitrophenol, picramic acid, 1,2-diamino-4-nitrobenzene, 1,4-diamino-2-nitrobenzene, 3-nitro-4-aminophenol, 1-hydroxy-2-amino-3-nitrobenzene, 2-hydroxyethylpicramic acid, 3-nitro-p-hydroxyethylaminophenol, 4-hydroxypropylamino-3-nitrophenol, and N,N-bis(2-hydroxyethyl)-2'-nitro-p-phenylenediamine.

(Surfactant)

The powder hair dye composition of the present invention can further contain an anionic surfactant, a nonionic surfactant, an amphoteric surfactant and/or a cationic surfactant from the viewpoint of imparting good miscibility with other agents. In addition, cationic surfactants have the same advantages as other surfactants, and simultaneously also contribute as a conditioning component.

Examples of anionic surfactants include sulfate, sulfonate, carboxylate and phosphate type anionic surfactants. More specifically, C10-18 alkyl sulfates and their ether sulfates are preferable. As the alkyl ether sulfates, a C12-14 alkyl ether sulfate is preferable, and a lauryl ether sulfate is more preferable, and among these, one having one to four ethyleneoxide group(s) in a molecule is further preferable. Examples of anionic surfactants also include fatty acid amide sulfates, and long-chain mono- and di-alkyl phosphates. Among these, an alkyl sulfate is preferable, and a lauryl sulfate is more preferable.

Examples of nonionic surfactants include long-chain fatty acid mono- and di-alkanolamides such as coconut mono- or di-ethanolamide, myristic acid mono- or di-ethanolamide, stearic acid mono- or di-ethanolamide; alkylpolyglucosides having a C8-18 alkyl group and one to five glucoside unit(s); sorbitan esters such as polyethylene glycol sorbitan stearic acid, palmitic acid, myristic acid and lauric acid ester; fatty acid polyglycol esters; a polycondensate of ethylene oxide and propylene oxide commercially available under the trade name of "Pluronic (registered trademark)"; polyoxyethylene alkyl ethers (the number of carbons in the alkyl group is preferably from 10 to 22, the number of moles added of polyoxyethylene per molecule is preferably from about 2.5 to about 100, and more preferably from about 10 to about 30).

Preferable amphoteric surfactants include various known betaines such as alkylbetaines, fatty acid amide alkylbetaines, and sulfobetaines like laurylhydroxy sulfobetaine, long-chain alkyl amino acids such as cocoaminoacetate, cocoamino-propionate, sodium cocoamphopropionate, and sodium cocoamphoacetate.

Examples of suitable cationic surfactants include a mono- or di-long-chain alkyl quaternary ammonium salt of the following general formula:

[Chem. 3]

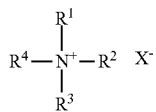

In the formula, $R^1$ represents a saturated or unsaturated linear or branched C8-22 alkyl group, or a group represented by $R^5CONH(CH_2)_n-$ or $R^5COO(CH_2)_n-$ ($R^5$ represents a saturated or unsaturated linear or branched C7-21 alkyl group, and n represents a number from 1 to 4), $R^2$ represents a hydrogen atom, a saturated or unsaturated linear or branched C1-22 alkyl group, or a group represented by the $R^5CONH(CH_2)_n-$ or $R^5COO(CH_2)_n-$, $R^3$ and $R^4$ represent a hydrogen atom or a C1-4 lower alkyl group, and X represents a chloride ion, a bromide ion or a methosulfate ion.

Specific examples of the above cationic surfactant include cetrimonium chloride, steartrimonium chloride, behentrimonium chloride, dipalmitoyl dimonium chloride, distearyl dimonium chloride, stearamidopropyltrimonium chloride, dioleoylethyl dimonium methosulfate, and dioleoylethyl hydroxyethylmonium methosulfate.

The content of surfactant in the powder hair dye composition of the present invention is preferably 0.1 mass % or more, more preferably 0.2 mass % or more, and further preferably 0.5 mass % or more from the viewpoint of imparting good miscibility with other agents, and also preferably 30 mass % or less, more preferably 20 mass % or less, and further preferably 15 mass % or less from the viewpoint of processibility into a powder form.

(Thickening Agent)

The powder hair dye composition of the present invention preferably further contains a synthetic polymeric compound, a semisynthetic polymeric compound or a natural polymeric compound as a thickening agent from the viewpoint of imparting good miscibility with other agents. Examples of synthetic polymeric compounds, semisynthetic polymeric compounds and natural polymeric compounds include (vinylpyrrolidone/dimethylaminoethyl methacrylate) copolymers (e.g., Copolymer 845, Copolymer 937, Copolymer 958; ISP Japan Ltd.), guar hydroxypropyltrimonium chloride (e.g., Rhaball gum CG-M, Rhaball Gum CG-6L, Rhaball Gum CG-M7, Rhaball Gum CG-M8M; Sumitomo Dainippon Pharma Co., Ltd., Jaguar C-13S, Jaguar C-14S, Jaguar C-17, Jaguar C-210, Jaguar C-162; Solvay Nicca, Ltd.), cationic dextran (e.g., CDC, CDC-H, CDC-L; Meito Sangyo Co., Ltd.), methyl cellulose (e.g., METOLOSE SM; Shin-Etsu Chemical Co., Ltd.), ethyl cellulose (e.g., EMUL-FREE CBG; IKEDA CORPORATION), hydroxyethyl cellulose (e.g., Cellosize QP4400H, QP52000H; Dow Chemical Japan, Ltd., SE-600, SE-850; Daicel Corporation), hydroxypropyl cellulose (e.g., NISSO HPC-H, HPC-M; Nippon Soda Co., Ltd.), carboxymethyl cellulose (e.g., CMC DAICEL 1380; Daicel FineChem Ltd.), hydroxypropyl xanthan gum (e.g., Rhaball Gum EX; Sumitomo Dainippon Pharma Co., Ltd.), pullulan (e.g., Pullulan PF-20, Pullulan PI-20; HAYASHIBARA CO., LTD.), and xanthan gum (e.g., Echo gum; Sumitomo Dainippon Pharma Co., Ltd.)

These thickening agents can be used individually or two or more thickening agents can be used in combination. The content of the thickening agent in the powder hair dye composition of the present invention is preferably 0.05 mass % or more, more preferably 0.1 mass % or more, and further preferably 0.5 mass % or more from the viewpoint of imparting good miscibility with other agents, and also preferably 20 mass % or less, more preferably 10 mass % or less, and further preferably 5 mass % or less from the same viewpoint.

(Oily Component)

The powder hair dye composition of the present invention preferably contains an oily component from the viewpoint of preventing the composition from scattering when the composition is being handled. Examples of oily components can include hydrocarbon oils, animal and vegetable fats and oils, polyolefins, higher fatty acids, fatty acid esters, fatty acid amides, and their mixtures. Among these, hydrocarbon oils are preferable, and liquid paraffin is more preferable. The content of the oily component in the powder hair dye composition of the present invention is preferably 0.01 mass % or more, more preferably 0.1 mass % or more, further preferably 1.0 mass % or more, and further preferably 2.0 mass % or more from the viewpoint of preventing powders from scattering when the composition is being handled, and also preferably 20 mass % or less, and more preferably 10 mass % or less from the viewpoint of the flow properties of powder and ease of handling.

(Other Optional Components)

To the powder hair dye composition of the present invention, other components which are commonly used as cosmetic materials can be further added as long as the powder form and function as a hair dye are maintained. Examples of such optional components can include antiseptic agents, sequestering agents, stabilizing agents, antioxidants, ultraviolet absorbing agents, moisturizing agents, and odor-control agents, and specific examples of optional components include hydrolyzed proteins, protein derivatives, amino acids, botanical extract, vitamins, pigments, and perfumes.

(Manufacturing Method)

The powder hair dye composition of the present invention may be manufactured, for example, by mixing the components (A), (B) and (C), and optionally other optional component(s). Any universal mixer can be used for mixing, and a mixer having a high stirring force is preferable from the viewpoint of mixing properties for the components (A), (B) and (C). Examples of preferable mixers include, Henschel mixer.

(Method for Use)

The powder hair dye composition of the present invention may be mixed with a composition containing hydrogen peroxide and/or an alkaline agent just before use and then the mixture may be applied to hair, for hair dyeing. The powder hair dye composition of the present invention may be mixed with a two-part oxidation hair dye composition or a hair dye composition containing another direct dye, for hair dyeing. The powder hair dye composition of the present invention may be mixed with a shampoo, a hair conditioner, or a hair treatment for use.

With respect to the embodiments described above, preferable aspects of the present invention will now be further disclosed.

<1>

A powder hair dye composition comprising the following components (A) to (C):

(A) 3.0 to 20 mass % of one or more azo dyes selected from the group consisting of the following (A-1), (A-2) and (A-3),

[Chem. 4]

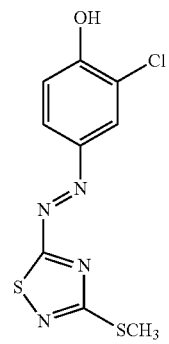

(A-1)

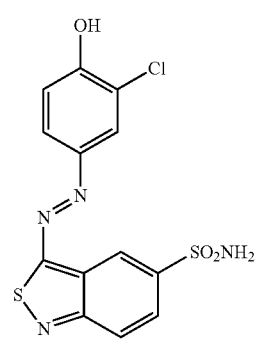

(A-2)

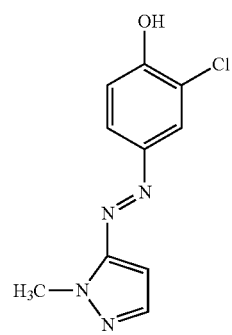

(A-3)

(B) an alkaline agent other than alkanolamines, and
(C) 1.5 mass % or more and 40 mass % or less of solvent.

<2>

A powder hair dye composition comprising the following components (A) to (C):

(A) one or more azo dyes selected from the group consisting of the following (A-1), (A-2) and (A-3),

[Chem. 5]

(A-1)

(A-2)

(A-3)

(B) 1.5 mass % or more and 20 mass % or less of alkaline agent other than alkanolamines, and (C) 1.5 mass % or more and 40 mass % or less of solvent.

<3>

A powder hair dye composition comprising the following components (A) to (C):

(A) one or more azo dyes selected from the group consisting of the following (A-1), (A-2) and (A-3),

[Chem. 6]

(A-1)

(A-2)

(A-3)

(B) one of two or more alkaline agents selected from metasilicates, alkali metal hydroxides, alkaline earth metal hydroxides, alkanediamines or salts thereof, carbonates and hydrogencarbonates, and (C) 1.5 mass % or more and 40 mass % or less of solvent.

<4>

A powder hair dye composition comprising the following components (A) to (C):

(A) one or more azo dyes selected from the group consisting of the following (A-1), (A-2) and (A-3),

[Chem.7]

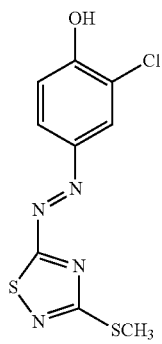
(A-1)

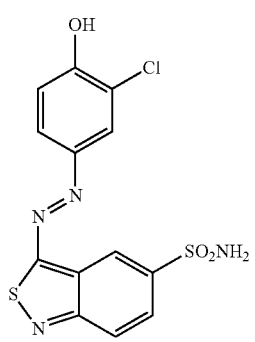
(A-2)

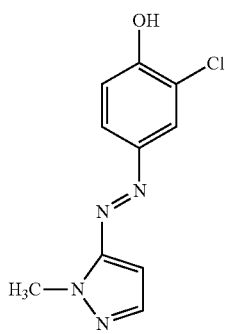
(A-3)

(B) an alkaline agent other than alkanolamines, and (C) 5 mass % or more and 35 mass % or less of solvent.

<5>

A powder hair dye composition comprising the following components (A) to (C):

(A) 3.0 mass % or more and 20 mass % or less of one or more azo dyes selected from the group consisting of the following (A-1), (A-2) and (A-3),

[Chem.8]

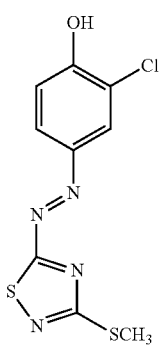
(A-1)

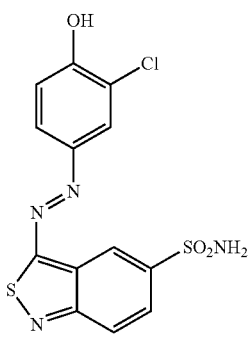
(A-2)

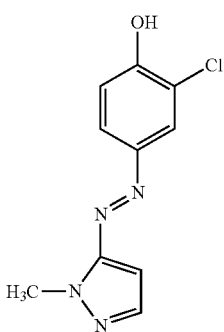
(A-3)

(B) 1.5 mass % or more and 20 mass % or less of alkaline agent other than alkanolamines, and (C) 5 mass % or more and 35 mass % or less of solvent.

<6>

A powder hair dye composition comprising the following components (A) to (C):

(A) 3.0 mass % or more and 20 mass % or less of one or more azo dyes selected from the group consisting of the following (A-1), (A-2) and (A-3),

[Chem.9]

(A-1)
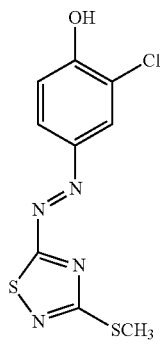

(A-2)
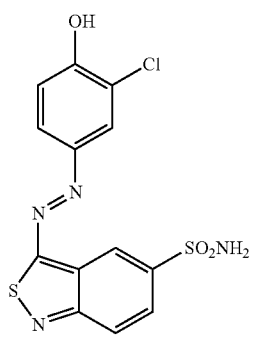

(A-3)
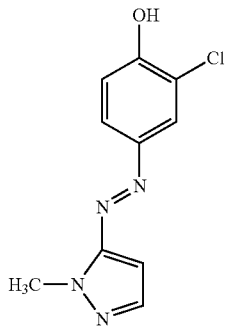

(B) 1.5 mass % or more and 20 mass % or less of one or more alkaline agents selected from metasilicates, alkali metal hydroxides, alkaline earth metal hydroxides, alkanediamines or salts thereof, carbonates, and hydrogencarbonates, and (C) 5 mass % or more and 35 mass % or less of solvent.

<7>

The powder hair dye composition according to any one of <1> to <6>, where the content of component (A) is 0.1 to 50 mass %, preferably 0.5 to 30 mass %, more preferably 1.0 to 20 mass %, further preferably 3.0 to 20 mass %, and further preferably 5.0 to 20 mass %.

<8>

The powder hair dye composition according to any one of <1>, <2>, <4>, <5> and <7>, where the component (B) is one or more selected from metasilicates, alkali metal hydroxides, alkaline earth metal hydroxides, alkanediamines or salts thereof, carbonates, and hydrogencarbonates.

<9>

The powder hair dye composition according to any one of <1> to <8>, where the content of component (B) is 0.1 to 40 mass %, preferably 0.2 to 30 mass %, more preferably 0.3 to 25 mass %, further preferably 0.5 to 20 mass %, further preferably 1.0 to 20 mass %, and further preferably 1.5 to 20 mass %.

<10>

The powder hair dye composition according to any one of <1> to <9>, where the component (C) is water or a water-soluble organic solvent selected from methanol, ethanol, n-propanol, isopropanol, n-butanol, isobutanol, ethylene glycol, propylene glycol, dipropylene glycol, 1,3-butylene glycol, ethylene glycol monoethyl ether, acetone, diethyl ether, tetrahydrofuran, and diacetone alcohol, or a mixture of water and a water-soluble organic solvent.

<11>

The powder hair dye composition according to any one of <1> to <10>, where the content of component (C) is from 2 to 35 mass %, preferably from 3 to 30 mass %, and more preferably from 5 to 25 mass %.

<12>

The powder hair dye composition according to any one of <1> to <11>, further containing component (D), a powder carrier.

<13>

The powder hair dye composition according to <12>, where the components (A), (B) and (C) are carried by the component (D).

EXAMPLES

Examples 1 to 3 and Comparative Examples 1 to 3

First, solid components, component (A), carboxymethyl cellulose and EDTA 4Na, of components shown in Table 1 were uniformly stirred and mixed. Next, liquid components, liquid paraffin, 48 mass % sodium hydroxide aqueous solution and component (C), were added gradually so that lumps were not generated, and the obtained mixture was stirred to prepare a uniform powder hair dye composition. Hair dyeing was carried out with each hair dye composition in accordance with the following hair dyeing method, and a color of each hair dye composition per se and a color of hair after hair dyeing were subjected to comparison in accordance with the following color evaluation method. It should be noted that 48 mass % sodium hydroxide aqueous solution was blended in a hair dye composition in an amount of 5 mass %; however the active amount was shown in Table 1.

Examples 4 to 15

A powder hair dye composition was prepared in the same manner as in Examples 1 to 3 except that the component (B) in Examples 1 to 3 was changed to compounds described in Table 2. It should be noted that a color of hair when hair was dyed by a powder hair dye composition using (A-1), (A-2) or (A-3) is not affected by the type of component (B), and thus hair after hair dyeing was not evaluated in Examples 4 to 15, and values of hair after hair dyeing and a color of each hair dye composition itself corresponding to (A-1), (A-2) or (A-3) in Examples 1 to 3 were used for comparison.

Examples 16 to 24, and Comparative Examples 4 to 6

A powder hair dye composition was prepared in the same manner as in Examples 1 to 3 except that the content of component (C) in Examples 1 to 3 was changed to amounts shown in Table 3, and the component (B) in Examples 18, 21 and 24 was replaced with potassium hydroxide. Hair after hair dyeing and colors of respective hair dye compositions per se in Examples and Comparative Examples were subjected to comparison in the same manner as in Examples 4 to 15.

(Hair Dyeing Method)

To 0.15 g of powder hair dye composition shown in Tables 1 to 3, 9.85 g of 1.68 mass % aqueous solution of ammonia was added, and the obtained mixture was stirred until being uniform for about a minute with a spatula to prepare a hair dye mixed solution. To about 1 g of untreated gray hair bundle purchased from Beaulax Co., Ltd., 1.0 g of hair dye mixed solution was applied and spread by rubbing with hands over a minute. The hair was allowed to stand at 30° C. for 20 minutes, rinsed with about 40° C. water for 30 seconds, wiped with a towel, and dried with a drier.

(Color Evaluation Method for Powder Hair Dye Composition)

In a cylindrical container with a diameter of 2.5 cm and a depth of 1 cm, about 0.8 g of powder hair dye composition was put, the surface was uniformly leveled with a spatula. A glass slide with a thickness of about 1 mm was then put thereon, and measurement was carried out from above the glass slide using a color-difference meter (CR-400 Chroma Meter manufactured by KONICA MINOLTA Sensing) by the CIE colorimetric system (L*,a*,b*,h).

(Hair Color Evaluation Method)

The hue of a hair bundle immediately after being treated with the hair dye mixture, washed and dried was measured using a color-difference meter by the CIE colorimetric system (L*,a*,b*,h), and the color difference (ΔE*) and hue difference (Δh) from the above powder hair dye composition were calculated by the following formula.

$$\Delta E^* = \sqrt{(L^*_1 - L^*_0)^2 + (a^*_1 - a^*_0)^2 + (b^*_1 - b^*_0)^2} \quad [\text{Math.1}]$$

where $L^*_0$, $a^*_0$ and $b^*_0$ represent values of L*, a* and b*, respectively, of a powder hair dye composition, and $L^*_1$, $a^*_1$ and $b^*_1$ represent values of L*, a* and b*, respectively, of hair immediately after hair dyeing.

$$\Delta h = h_1 - h_0$$

where $h_0$ represent a h value of a powder hair dye composition, and $h_1$ represents a h value of hair immediately after hair dyeing. The h value is a hue angle and 0°=360°. Because of this, when Δh is above 180, a value of 360−Δh is taken.

TABLE 1

| | | | Example 1 | Comparative Example 1 | Example 2 | Comparative Example 2 | Example 3 | Comparative Example 3 |
|---|---|---|---|---|---|---|---|---|
| Composition (mass %) | (A) | (A-1) (HC Blue 18) | 16.7 | 16.7 | — | — | — | — |
| | | (A-2) (HC Red 18) | — | — | 16.7 | 16.7 | — | — |
| | | (A-3) (HC Yellow 16) | — | — | — | — | 16.7 | 16.7 |
| | (B) | Sodium hydroxide | 2.4 | — | 2.4 | — | 2.4 | — |
| | (D) | Cornstarch*[1] | 3.8 | 3.8 | 3.8 | 3.8 | 3.8 | 3.8 |
| | | Silicon dioxide*[2] | 44.6 | 47.0 | 44.6 | 47.0 | 44.6 | 47.0 |
| | Others | Liquid paraffin*[3] | 7.1 | 7.1 | 7.1 | 7.1 | 7.1 | 7.1 |
| | | Carboxymethyl cellulose*[4] | 2.1 | 2.1 | 2.1 | 2.1 | 2.1 | 2.1 |
| | | EDTA 4Na | 1.5 | 1.5 | 1.5 | 1.5 | 1.5 | 1.5 |
| | (C) | Water | 21.8 | 21.8 | 21.8 | 21.8 | 21.8 | 21.8 |
| | | Total | 100.0 | 100.0 | 100.0 | 100.0 | 100.0 | 100.0 |
| Evaluation | | (L*, a*, b*, h) of powder | L*: 31.66 a*: 2.44 b*: −0.5 h: 348.47 | L*: 48.85 a*: 17.10 b*: 7.83 h: 24.60 | L*: 31.1 a*: 31.85 b*: 10.24 h: 17.82 | L*: 44.28 a*: 30.10 b*: 17.01 h: 29.48 | L*: 76.57 a*: 8.87 b*: 54.36 h: 80.73 | L*: 84.26 a*: 0.06 b*: 39.58 h: 89.91 |
| | | (L*, a*, b*, h) of hair after hair dyeing | L*: 34.78 a*: 8.64 b*: −14.79 h: 300.31 | L*: 35.73 a*: 8.30 b*: −14.54 h: 299.73 | L*: 35.68 a*: 54.21 b*: 16.8 h: 17.21 | L*: 34.61 a*: 54.53 b*: 17.58 h: 17.87 | L*: 67.27 a*: 9.43 b*: 69.96 h: 82.32 | L*: 68.52 a*: 6.35 b*: 63.71 h: 84.31 |
| | | dh | −48.0 | 84.9 | −1.0 | −11.6 | 2.0 | −5.6 |
| | | dE* | 15.9 | 27.4 | 23.7 | 26.3 | 18.2 | 29.5 |

TABLE 2

| | | | Examples | | | | | |
|---|---|---|---|---|---|---|---|---|
| | | | 4 | 5 | 6 | 7 | 8 | 9 |
| Composition (mass %) | (A) | (A-1) (HC Blue 18) | 16.7 | 16.7 | 16.7 | 16.7 | — | — |
| | | (A-2) (HC Red 18) | — | — | — | — | 16.7 | 16.7 |
| | | (A-3) (HC Yellow 16) | — | — | — | — | — | — |
| | (B) | Potassium hydroxide | 2.4 | — | — | — | 2.4 | — |
| | | Sodium metasilicate | — | 2.4 | — | — | — | 2.4 |
| | | Sodium carbonate | — | — | 2.4 | — | — | — |
| | | Calcium hydroxide | — | — | — | 2.4 | — | — |
| | (D) | Cornstarch*[1] | 3.8 | 3.8 | 3.8 | 3.8 | 3.8 | 3.8 |
| | | Silicon dioxide*[2] | 44.6 | 44.6 | 44.6 | 44.6 | 44.6 | 44.6 |
| | Others | Liquid paraffin*[3] | 7.1 | 7.1 | 7.1 | 7.1 | 7.1 | 7.1 |
| | | Carboxymethyl cellulose*[4] | 2.1 | 2.1 | 2.1 | 2.1 | 2.1 | 2.1 |

TABLE 2-continued

|  |  |  | | | | | | |
|---|---|---|---|---|---|---|---|---|
|  |  | EDTA 4Na | 1.5 | 1.5 | 1.5 | 1.5 | 1.5 | 1.5 |
|  | (C) | Water | 21.8 | 21.8 | 21.8 | 21.8 | 21.8 | 21.8 |
|  |  | Total | 100.0 | 100.0 | 100.0 | 100.0 | 100.0 | 100.0 |
| Evaluation |  | (L*, a*, b*, h) of powder | L*: 35.28 a*: 1.53 b*: −2.74 h: 299.22 | L*: 44.50 a*: 4.96 b*: 0.06 h: 0.71 | L*: 36.48 a*: 3.11 b*: 0.42 h: 7.68 | L*: 32.33 a*: 1.67 b*: 0.19 h: 6.37 | L*: 33.58 a*: 31.33 b*: 10.37 h: 18.31 | L*: 36.11 a*: 31.85 b*: 10.13 h: 17.64 |
|  |  | (L*, a*, b*, h) of hair after hair dyeing | L*: 34.78 a*: 8.64 b*: −14.79 h: 300.31 | L*: 34.78 a*: 8.64 b*: −14.79 h: 300.31 | L*: 34.78 a*: 8.64 b*: −14.79 h: 300.31 | L*: 34.78 a*: 8.64 b*: −14.79 h: 300.31 | L*: 35.68 a*: 54.21 b*: 16.8 h: 17.21 | L*: 35.68 a*: 54.21 b*: 16.8 h: 17.21 |
|  |  | dh | 1.1 | 60.4 | 67.4 | 66.1 | −1.1 | −0.4 |
|  |  | dE* | 13.5 | 17.6 | 15.7 | 16.2 | 23.8 | 23.3 |

|  |  |  | Examples | | | | | |
|---|---|---|---|---|---|---|---|---|
|  |  |  | 10 | 11 | 12 | 13 | 14 | 15 |
| Composition (mass %) | (A) | (A-1) (HC Blue 18) | — | — | — | — | — | — |
|  |  | (A-2) (HC Red 18) | 16.7 | 16.7 | — | — | — | — |
|  |  | (A-3) (HC Yellow 16) | — | — | 16.7 | 16.7 | 16.7 | 16.7 |
|  | (B) | Potassium hydroxide | — | — | 2.4 | — | — | — |
|  |  | Sodium metasilicate | — | — | — | 2.4 | — | — |
|  |  | Sodium carbonate | 2.4 | — | — | — | 2.4 | — |
|  |  | Calcium hydroxide | — | 2.4 | — | — | — | 2.4 |
|  | (D) | Cornstarch*1 | 3.8 | 3.8 | 3.8 | 3.8 | 3.8 | 3.8 |
|  |  | Silicon dioxide*2 | 44.6 | 44.6 | 44.6 | 44.6 | 44.6 | 44.6 |
|  | Others | Liquid paraffin*3 | 7.1 | 7.1 | 7.1 | 7.1 | 7.1 | 7.1 |
|  |  | Carboxymethyl cellulose*4 | 2.1 | 2.1 | 2.1 | 2.1 | 2.1 | 2.1 |
|  |  | EDTA 4Na | 1.5 | 1.5 | 1.5 | 1.5 | 1.5 | 1.5 |
|  | (C) | Water | 21.8 | 21.8 | 21.8 | 21.8 | 21.8 | 21.8 |
|  |  | Total | 100.0 | 100.0 | 100.0 | 100.0 | 100.0 | 100.0 |
| Evaluation |  | (L*, a*, b*, h) of powder | L*: 36.90 a*: 32.82 b*: 10.86 h: 18.32 | L*: 35.71 a*: 30.49 b*: 10.86 h: 19.61 | L*: 58.73 a*: 5.70 b*: 46.88 h: 83.07 | L*: 66.65 a*: 8.34 b*: 49.10 h: 80.36 | L*: 74.20 a*: 6.56 b*: 46.01 h: 81.89 | L*: 64.61 a*: 10.48 b*: 51.12 h: 78.42 |
|  |  | (L*, a*, b*, h) of hair after hair dyeing | L*: 35.68 a*: 54.21 b*: 16.8 h: 17.21 | L*: 35.68 a*: 54.21 b*: 16.8 h: 17.21 | L*: 67.27 a*: 9.43 b*: 69.96 h: 82.32 | L*: 67.27 a*: 9.43 b*: 69.96 h: 82.32 | L*: 67.27 a*: 9.43 b*: 69.96 h: 82.32 | L*: 67.27 a*: 9.43 b*: 69.96 h: 82.32 |
|  |  | dh | −1.1 | −2.4 | −0.8 | 2.0 | 0.4 | 3.9 |
|  |  | dE* | 22.2 | 24.4 | 24.9 | 20.9 | 25.1 | 19.1 |

TABLE 3

|  |  |  | Comparative Example | Examples | | | Comparative Example | Examples |
|---|---|---|---|---|---|---|---|---|
|  |  |  | 4 | 16 | 17 | 18 | 5 | 19 |
| Composition (mass %) | (A) | (A-1) (HC Blue 18) | 16.7 | 16.7 | 16.7 | 16.7 | — | — |
|  |  | (A-2) (HC Red 18) | — | — | — | — | 16.7 | 16.7 |
|  |  | (A-3) (HC Yellow 16) | — | — | — | — | — | — |
|  | (B) | Potassium hydroxide | — | — | — | 2.4 | — | — |
|  |  | Sodium metasilicate | 2.4 | 2.4 | 2.4 | — | 2.4 | 2.4 |
|  | (D) | Cornstarch*1 | 3.8 | 3.8 | 3.8 | 3.8 | 3.8 | 3.8 |
|  |  | Silicon dioxide*2 | 66.4 | 63.4 | 61.4 | 31.4 | 66.4 | 63.4 |
|  | Others | Liquid paraffin*3 | 7.1 | 7.1 | 7.1 | 7.1 | 7.1 | 7.1 |
|  |  | Carboxymethyl cellulose*4 | 2.1 | 2.1 | 2.1 | 2.1 | 2.1 | 2.1 |
|  |  | EDTA 4Na | 1.5 | 1.5 | 1.5 | 1.5 | 1.5 | 1.5 |
|  | (C) | Water | 0.0 | 3.0 | 5.0 | 35.0 | 0.0 | 3.0 |
|  |  | Total | 100.0 | 100.0 | 100.0 | 100.0 | 100.0 | 100.0 |
|  |  | (L*, a*, b*, h) of powder | L*: 58.53 a*: 21.60 b*: 9.82 h: 24.43 | L*: 40.97 a*: 7.45 b*: 0.48 h: 3.70 | L*: 37.29 a*: 7.07 b*: −0.80 h: 353.51 | L*: 32.72 a*: 0.59 b*: −0.51 h: 318.89 | L*: 49.29 a*: 21.12 b*: 21.12 h: 33.60 | L*: 38.64 a*: 30.00 b*: 11.17 h: 20.42 |
|  |  | (L*, a*, b*, h) of hair after hair dyeing | L*: 34.78 a*: 8.64 b*: −14.79 h: 300.31 | L*: 34.78 a*: 8.64 b*: −14.79 h: 300.31 | L*: 34.78 a*: 8.64 b*: −14.79 h: 300.31 | L*: 34.78 a*: 8.64 b*: −14.79 h: 300.31 | L*: 35.68 a*: 54.21 b*: 16.8 h: 17.21 | L*: 35.68 a*: 54.21 b*: 16.8 h: 17.21 |
|  |  | dh | 84.1 | 63.4 | 53.2 | −8.6 | −16.4 | −3.2 |
|  |  | dE* | 36.2 | 16.0 | 13.7 | 16.0 | 26.6 | 25.0 |

TABLE 3-continued

| | | | Examples | | Comparative Example | Examples | | |
|---|---|---|---|---|---|---|---|---|
| | | | 20 | 21 | 6 | 22 | 23 | 24 |
| Composition (mass %) | (A) | (A-1) (HC Blue 18) | — | — | — | — | — | — |
| | | (A-2) (HC Red 18) | 16.7 | 16.7 | — | — | — | — |
| | | (A-3) (HC Yellow 16) | — | — | 16.7 | 16.7 | 16.7 | 16.7 |
| | (B) | Potassium hydroxide | — | 2.4 | — | — | — | 2.4 |
| | | Sodium metasilicate | 2.4 | — | 2.4 | 2.4 | 2.4 | — |
| | (D) | Cornstarch*1 | 3.8 | 3.8 | 3.8 | 3.8 | 3.8 | 3.8 |
| | | Silicon dioxide*2 | 61.4 | 36.4 | 66.4 | 63.4 | 61.4 | 31.4 |
| | Others | Liquid paraffin*3 | 7.1 | 7.1 | 7.1 | 7.1 | 7.1 | 7.1 |
| | | Carboxymethyl cellulose*4 | 2.1 | 2.1 | 2.1 | 2.1 | 2.1 | 2.1 |
| | | EDTA 4Na | 1.5 | 1.5 | 1.5 | 1.5 | 1.5 | 1.5 |
| | (C) | Water | 5.0 | 30.0 | 0.0 | 3.0 | 5.0 | 35.0 |
| | | Total | 100.0 | 100.0 | 100.0 | 100.0 | 100.0 | 100.0 |
| ($L^*$, $a^*$, $b^*$, h) of powder | | | $L^*$: 36.67 | $L^*$: 33.62 | $L^*$: 79.02 | $L^*$: 77.16 | $L^*$: 74.21 | $L^*$: 64.33 |
| | | | $a^*$: 31.07 | $a^*$: 31.70 | $a^*$: 2.79 | $a^*$: 3.10 | $a^*$: 7.15 | $a^*$: 8.24 |
| | | | $b^*$: 10.34 | $b^*$: 11.41 | $b^*$: 43.17 | $b^*$: 53.36 | $b^*$: 50.15 | $b^*$: 47.10 |
| | | | h: 18.41 | h: 19.79 | h: 86.31 | h: 86.68 | h: 81.88 | h: 80.08 |
| ($L^*$, $a^*$, $b^*$, h) of hair after hair dyeing | | | $L^*$: 35.68 | $L^*$: 35.68 | $L^*$: 67.27 | $L^*$: 67.27 | $L^*$: 67.27 | $L^*$: 67.27 |
| | | | $a^*$: 54.21 | $a^*$: 54.21 | $a^*$: 9.43 | $a^*$: 9.43 | $a^*$: 9.43 | $a^*$: 9.43 |
| | | | $b^*$: 16.8 | $b^*$: 16.8 | $b^*$: 69.96 | $b^*$: 69.96 | $b^*$: 69.96 | $b^*$: 69.96 |
| | | | h: 17.21 | h: 17.21 | h: 82.32 | h: 82.32 | h: 82.32 | h: 82.32 |
| | | dh | −1.2 | −2.6 | −4.0 | −4.4 | 0.4 | 2.2 |
| | | $dE^*$ | 24.0 | 23.2 | 30.0 | 20.4 | 21.1 | 23.1 |

*1 Maize starch B (ROQUETTE)
*2 Kieselgur (Merck)
*3 HICALL K-350 (KANEDA Co., Ltd.)
*4 CMC Daicel 1380 (Daicel FineChem Ltd.)

The invention claimed is:

1. A powder hair dye composition, comprising:

(A at least one azo dye selected from the group consisting of the following (A-1), (A-2) and (A-3):

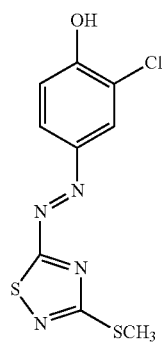

(A-1)

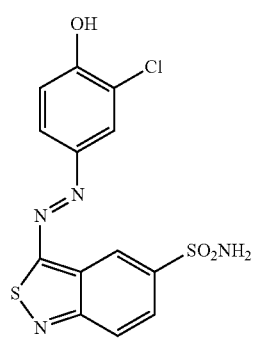

(A-2)

-continued

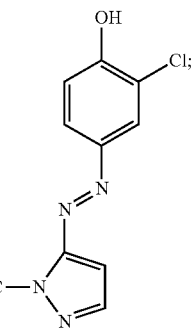

(A-3)

(B) an alkaline agent other than alkanolamines;
(C) 1.5 mass % or more and 40 mass % or less of solvent; and
(D) a powder carrier,
wherein the components (A), (B), and (C) are carried by the component (D).

2. The powder hair dye composition according to claim 1, wherein a content of the component (A) is 0.1 mass % or more and 50 mass % or less.

3. The powder hair dye composition according to claim 1, wherein the component (B) comprises at least one selected from the group consisting of metasilicates, alkali metal hydroxides, alkaline earth metal hydroxides, alkanediamines or salts thereof, carbonates, and hydrogen carbonates.

4. The powder hair dye composition according to claim 1, wherein a content of the component (B) is 0.1 mass % or more and 40 mass % or less.

5. The powder hair dye composition according to claim 1, wherein the component (C) is water or a water-soluble organic solvent comprising at least one selected from the group consisting of methanol, ethanol, n-propanol, isopropanol, n-butanol, isobutanol, ethylene glycol, propylene glycol, dipropylene glycol, 1,3-butylene glycol, ethylene glycol monoethyl ether, acetone, diethyl ether, tetrahydrofuran, and diacetone alcohol.

6. The powder hair dye composition according to claim 1, wherein a content of the component (C) is 2 mass % or more and 35 mass % or less.

7. The powder hair dye composition according to claim 1, wherein the component (D) comprises at least one selected from the group consisting of silica (silicon dioxide), diatomaceous earth, kaolin, bentonite, cornstarch, tapioca starch, rice starch, wheat starch, potato starch, nylon powder, montmorillonite, gypsum, sawdust, and pearlite.

8. The powder hair dye composition according to claim 1, wherein the component (D) comprises at least one selected from the group consisting of cornstarch, diatomaceous earth and silica.

9. The powder hair dye composition according to claim 1, wherein a content of the component (D) is 10 mass % or more and 90 mass % or less.

10. The powder hair dye composition according to claim 1, wherein a content of the component (D) is 40 mass % or more and 70 mass % or less.

11. The powder hair dye composition according to claim 1, further comprising a thickening agent at a content of 0.5 mass % or more and 5 mass % or less.

12. The powder hair dye composition according to claim 1, further comprising an oily component at a content of 2 to 10 mass %.

* * * * *